United States Patent [19]

Wheeler

[11] Patent Number: 5,941,860
[45] Date of Patent: Aug. 24, 1999

[54] FECAL POUCH AND INSTALLATION

[76] Inventor: Alton D. Wheeler, 3940 Fox Meadow La., Pasadena, Tex. 77504

[21] Appl. No.: 08/963,484

[22] Filed: Nov. 3, 1997

[51] Int. Cl.[6] .............................. A61M 1/00; A61F 5/44
[52] U.S. Cl. .......................... 604/327; 604/328; 604/331; 604/338; 604/345; 604/351; 604/353
[58] Field of Search ............................ 128/283; 600/32, 600/328, 30; 604/327, 328, 332, 339, 341, 351

[56] References Cited

U.S. PATENT DOCUMENTS

| | | | |
|---|---|---|---|
| 2,877,768 | 3/1959 | Higgins | 604/338 |
| 3,006,343 | 10/1961 | Baxter | 604/338 |
| 3,548,828 | 12/1970 | Vasile | 128/283 |
| 3,938,521 | 2/1976 | Ritota et al. | 128/283 |
| 4,210,131 | 7/1980 | Perlin | 128/1 |
| 4,319,573 | 3/1982 | Whitlock | 128/295 |
| 4,471,782 | 9/1984 | Shuffield | 128/341 |
| 4,950,223 | 8/1990 | Silvanov | 600/32 |
| 5,375,265 | 12/1994 | Selzer | 2/242 |
| 5,520,669 | 5/1996 | Mulholland | 604/328 |

*Primary Examiner*—John G. Weiss
*Assistant Examiner*—Miley C. Peppers, III
*Attorney, Agent, or Firm*—William W. Haefliger

[57] ABSTRACT

A fecal collector which comprises an elongated, flaccid pouch having an entrance end; an anchor attached to the pouch entrance end to anchor the entrance end in the lower bowel, and; a positioner attached to the pouch in spaced relation to the anchor O-ring, to remain outside the lower bowel and adjacent the body, for blocking tilting of the anchor in the bowel.

15 Claims, 5 Drawing Sheets

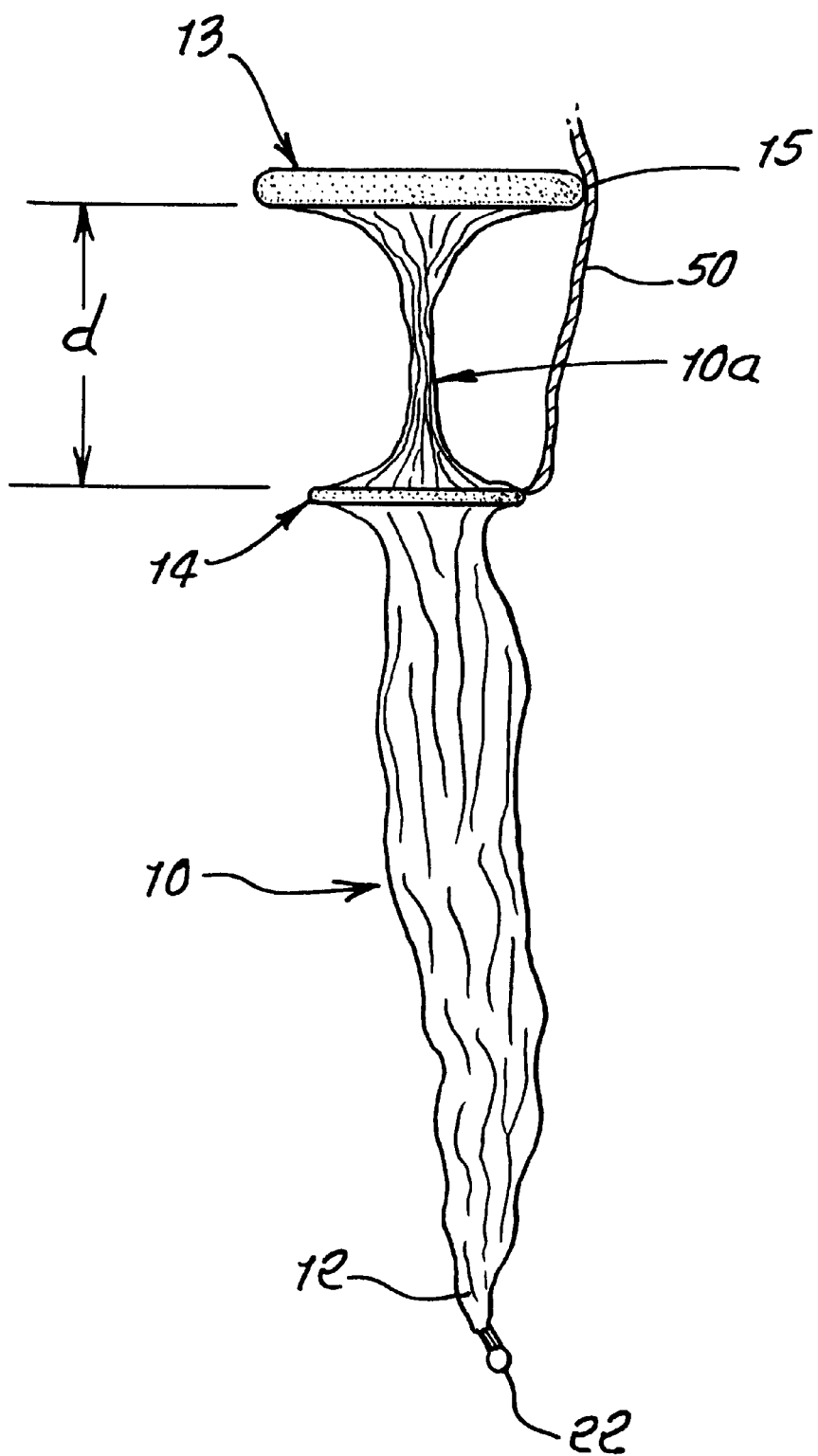

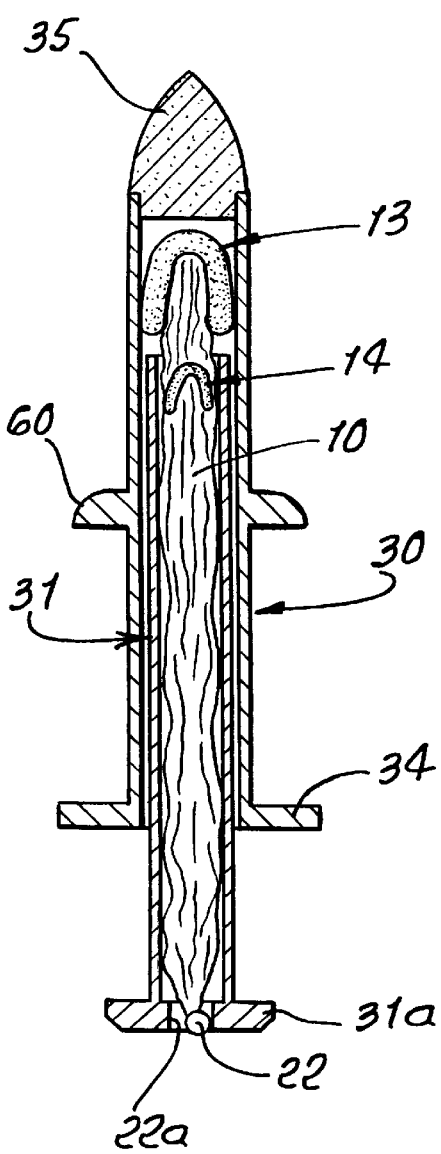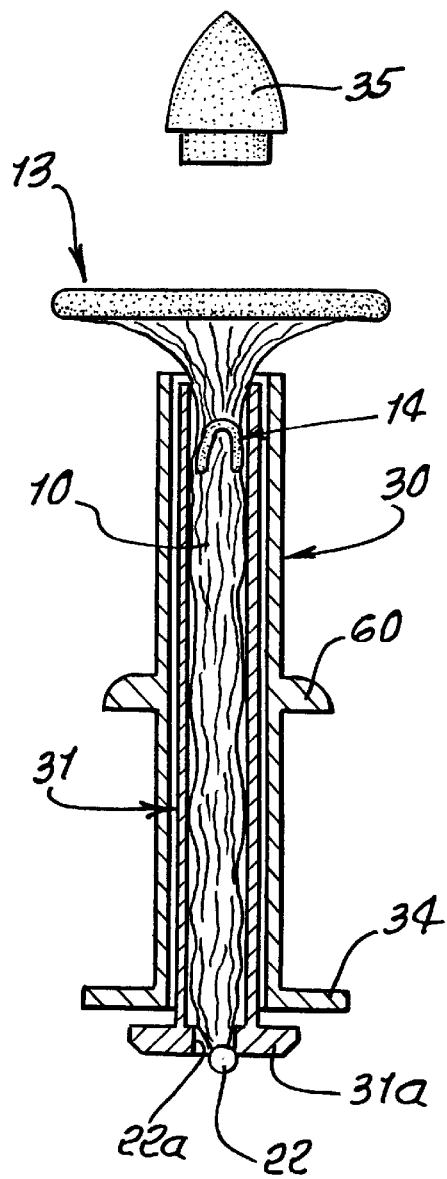

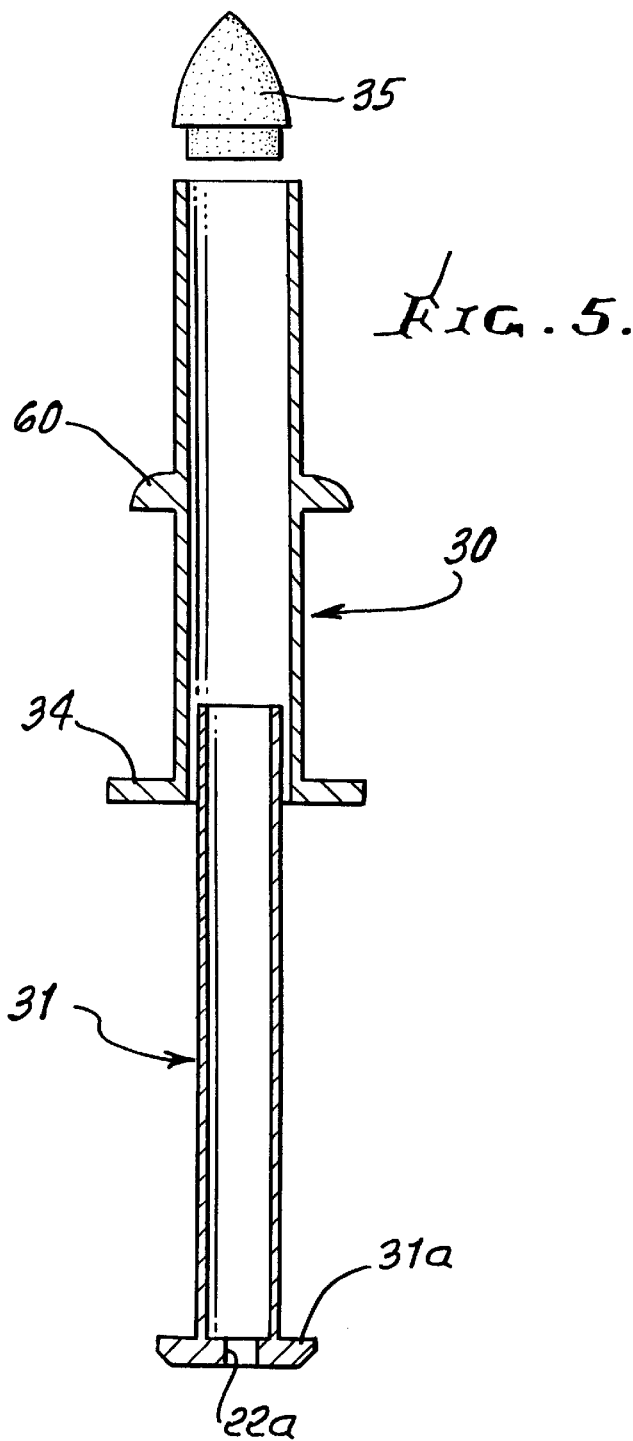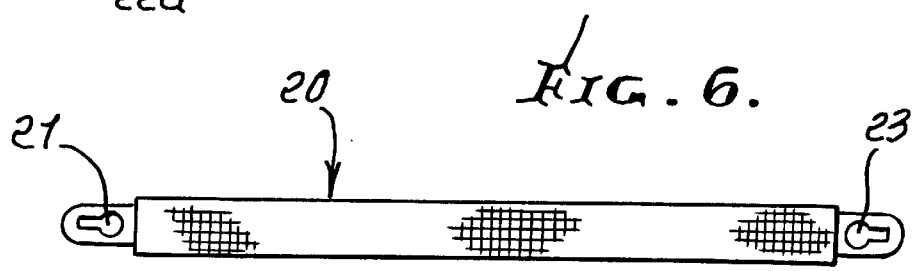

FECAL POUCH AND INSTALLATION

BACKGROUND OF THE INVENTION

This invention relates generally to in situ collection of fecal material, and more particularly, to simple and effective apparatus and method to facilitate such collection.

There is need for sanitary collection of fecal material, as for example in nursing homes where patients cannot move from their beds. There is also need for sanitary apparatus and method that improves over the common use of bedpans.

SUMMARY OF THE INVENTION

It is a major object of the invention to provide apparatus and method meeting the above need.

Basically, the fecal collecting apparatus of the invention comprises:

a) an elongated, flaccid pouch having an entrance end, b) an anchor attached to the pouch entrance end to anchor the entrance end in the lower bowel, and c) a positioner attached to the pouch in spaced relation to the anchor, to remain outside the lower bowel and adjacent the body, for blocking tilting of the anchor in the bowel.

As will be seen, at least one, and preferably both, of the anchor and positioner comprise resiliently and yieldably deformable O-rings, facilitating their installation and their comfortable use.

Another object of the invention is to provide a band attached to the pouch, after its lengthwise distension away from the anchor and positioner. The band may then be connected to a user's leg, to protectively locate the pouch adjacent the user's leg.

A further object is to provide the anchor O-ring to be yieldably and resiliently bendable and sized for reception in the lower bowel while in U-shaped, bent condition, and for resilient expansion into O-ring shape, annularly pushing against the bowel lining, for in-place retention.

In addition, the positioner O-ring is preferably resiliently bendable and is diametrically smaller than the anchor O-ring.

Yet another object is to provide apparatus to install a fecal collector, as referred to, and comprising:

d) an inserter tube having a forward portion to be endwise inserted into the lower bowel, e) a pusher tube slidable endwise in the inserter tube, f) the anchor received in the inserter tube to be pushed from that tube and into the bowel for installation in the lower bowel, by forward displacement of the pusher tube in the inserter tube, g) the positioner received in the pusher tube to be pulled from that tube upon retraction of both tubes following installation of the anchor in the lower bowel, and h) the pouch received in collapsed condition in the tubes.

Such apparatus enables the anchor O-ring to be retained in resiliently deformed condition in the inserter tube, and also the positioner O-ring to be retained in resiliently deformed condition in the pusher tube, to enable quick, safe installation.

Additional objects include provision of a gage flange on the inserter tube to engage the body and limit insertion of the inserter tube into the lower bowel; and provision of stop means on the tubes to limit the forward displacement of the pusher tube in the inserter tube.

These and other objects and advantages of the invention, as well as the details of an illustrative embodiment, will be more fully understood from the following specification and drawings, in which:

DRAWING DESCRIPTION

FIG. 2 is a side elevational view of the FIG. 1 apparatus;

FIG. 3 is an elevation showing apparatus to install the FIGS. 1 and 2 collector apparatus in the lower bowel;

FIG. 4 is like FIG. 3 but showing a partly installed condition of the collector apparatus;

FIG. 5 is an exploded view of components of the installation apparatus;

FIG. 6 is a plan view of a retention band; and

DETAILED DESCRIPTION

Figure 1:
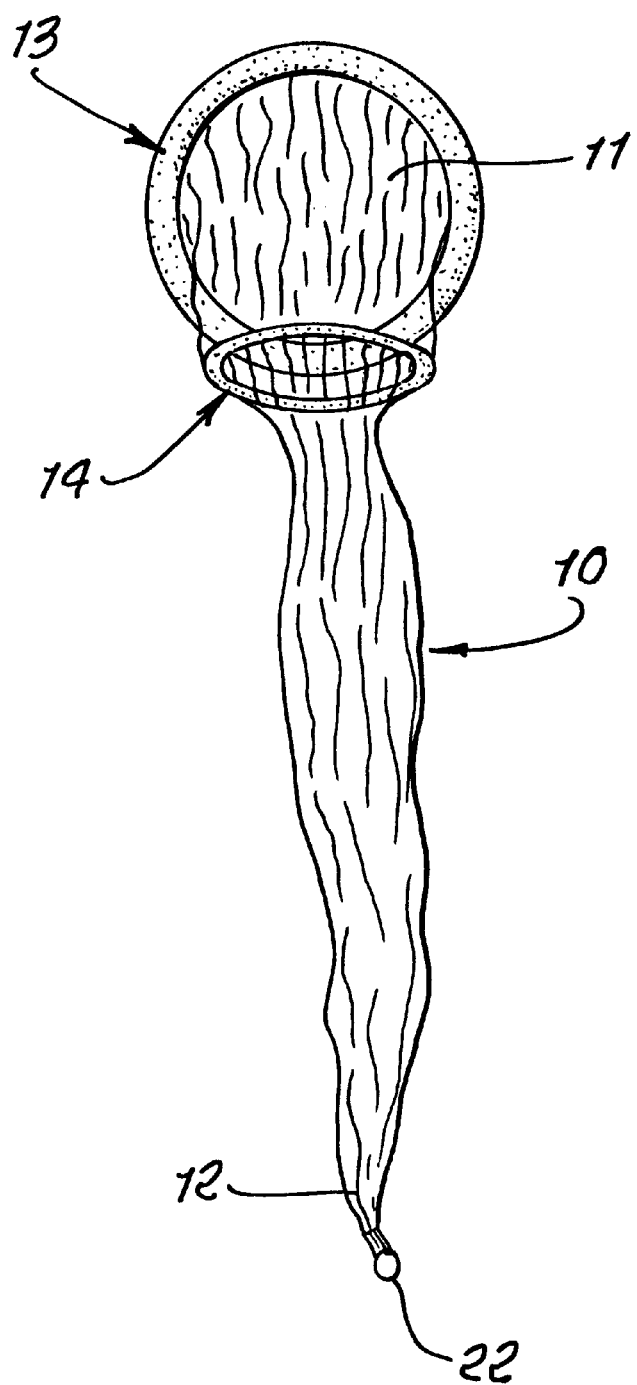
FIG. 1 is a view, partly in elevation, showing one preferred form of the collector apparatus of the invention.

In FIG. 1, an elongated, flaccid, feces collector pouch 10 has an entrance end 11, and a closed lower distal end 12. An anchor is attached to the pouch entrance end to anchor the entrance end in the lower bowel. Also, a positioner is attached to the pouch in spaced relation to the anchor O-ring, to remain outside the lower bowel and adjacent the body, for blocking tilting of the anchor in the bowel. At least one, and preferably both, of the anchor and positioner may consist of O-rings that are typically yieldably and resiliently deformable, as for example bendable. See anchor O-ring 13 and positioner O-ring 14 in undeformed condition in FIGS. 1 and 2, and deformed condition in FIG. 3.

In FIGS. 1 and 2, the elastomeric O-ring 13 surrounds the upper entrance end 11 of the flaccid pouch, and is attached to that upper end. O-ring 14 is attached to the side wall of the pouch, at a distance "d" from ring 13, so as to engage the body at the rectum and limit installation entry of the ring 13 in the lower bowel. Ring 14 is sized to gently but firmly compressively engage the lining 50 of the lower bowel, as at 15, to retain the pouch entrance end in position to receive and pass fecal material that then fills into the pouch. Distance "d" is, for example, about one inch, but may vary. Ring 14 also blocks or prevents tilting of installed ring 13, since the pouch annular extent 10a between the rings, and attached to the rings, acts to transmit force via 10a, tending to stabilize ring 13 in position, as seen in FIG. 2.

Figure 7:
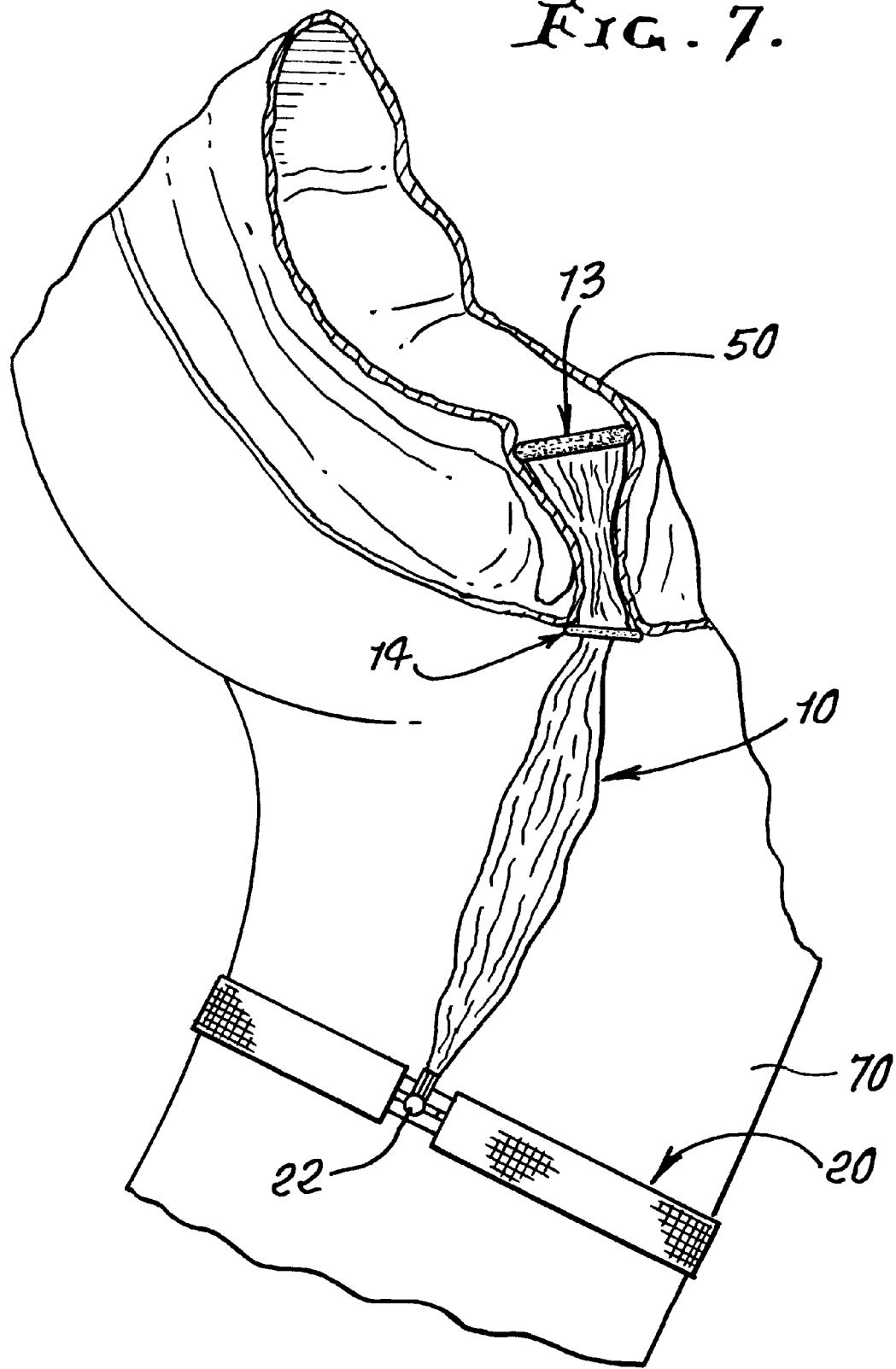
FIG. 7 is a view showing an installed condition of the collector apparatus.

FIG. 6 shows a band 20 connected to the pouch, in spaced relation to the positioner, for retaining the pouch to a user's leg 70, as seen in FIG. 7. A slot 21 in one end of the band hooks over a bead 22 at the pouch closed end; and the band may be encircled about the user's leg to enable a second slot 23 at the band opposite end to also hook over the bead. This enables band retention of the distended pouch close to the user's leg.

Apparatus is shown in FIGS. 3–5 to install the fecal collector, as described, as in FIG. 7 position. Such apparatus includes an inserter tube 30 having a forward portion to be endwise inserted into the lower bowel; and a pusher tube 31 slidable endwise in the inserter tube.

The anchor ring 13, in deformed condition, is received in the inserter tube to be pushed from that tube and into the bowel for installation in the lower bowel, by forward displacement of the pusher tube in the inserter tube; and the positioner O-ring in deformed condition is received in the pusher tube to be pulled from that tube upon retraction of both tubes following installation of the anchor in the lower bowel.

Note that the pouch 10 is received in collapsed condition in the tubes 30 and 31, as shown, for installation.

As the tube 31 is moved forwardly by manual pressure exerted at end 31a, the O-ring 13 is expelled from the upper end of tube 30, as seen in FIG. 4. A tapered plug 35 may be used at the end of the tube 30 to assist entry into the lower bowel. Plug 35 may consist of a wax or other substance that melts at body temperature (96°–100° F.). Flange 34 on tube 30 assists slidable pushing of tube 31 forward in tube 30. Gage flange 60 on tube 30 engages the body and limits tube 30 insertion. Engagement of flange 31a with flange 34 limits forward displacement of tube 31 in tube 30.

Upon retraction of the tubes, O-ring 14 is expelled from the forward end of tube 31, and assumes FIG. 2 configuration. Also, the pouch distends from tube 31, since bead 22 is retained in an opening 22a in flange 31a, and bead 22 is thereafter releasably freed from the lower end 31b of tube 31.

Removal of the feces-filled pouch from the bowel is achieved by tugging on O-ring 14 to pull ring 13 from the bowel, after which the pouch may be emptied and disposed of.

I claim:

1. A fecal collector comprising, in combination,
   a) an elongated, flaccid pouch having an entrance end,
   b) an anchor attached to the pouch entrance end for anchoring said entrance end in a lower bowel, and
   c) a positioner attached to the pouch in spaced relation to the anchor, for remaining outside a lower bowel, and for blocking tilting of the anchor in a bowel,
   d) and relatively movable inserter and pusher tubes respectively receiving said anchor and positioner for pushing the anchor from the insertion tube into a lower bowel and for discharge of the positioner from the pusher tube in response to retraction of both tubes relative to the anchor, the pouch received in collapsed condition in at least one of the tubes.

2. The combination of claim 1 wherein at least one of the anchor and positioner is an O-ring.

3. The combination of claim 1 wherein both the anchor and positioner are O-rings.

4. The combination of claim 3 wherein the anchor O-ring is larger than the positioner O-ring.

5. The combination of claim 3 wherein the positioner O-ring is spaced at least about one inch from the anchor O-ring.

6. The combination of claim 1 including a band connected to the pouch, in spaced relation to said positioner, for retaining the pouch to a user's leg.

7. The combination of claim 6 wherein the pouch has a closed end remote from said entrance end, and said band is connected to said pouch proximate said closed end.

8. The combination of claim 3 wherein said anchor O-ring is yieldably resiliently bendable and sized for reception in a lower bowel while in U-shaped, bent condition, and for resilient expansion into O-ring shape, annularly pushing against a bowel lining.

9. The combination of claim 8 wherein said positioner O-ring is resiliently bendable and is diametrically smaller than said anchor O-ring.

10. Apparatus to install a fecal collector, comprising:
    a) an elongated, flaccid pouch having an entrance end,
    b) an anchor attached to the pouch entrance end for anchoring said entrance end in a lower bowel, and
    c) a positioner attached to the pouch in spaced relation to the anchor for remaining outside a lower bowel, and for blocking tilting of the anchor in a bowel,
    d) an inserter tube having a forward portion to be endwise inserted into a lower bowel,
    e) a pusher tube slidable endwise in the inserter tube,
    f) said anchor received in the inserter tube to be pushed from that tube and into a bowel for installation in a lower bowel, by forward displacement of the pusher tube in the inserter tube,
    g) said positioner received in the pusher tube to be pulled from that tube upon retraction of both tubes following installation of the anchor in a lower bowel, and
    h) the pouch received in collapsed condition in said tubes.

11. The combination of claim 10 wherein the anchor is an O-ring retained in resiliently deformed condition in the inserter tube.

12. The combination of claim 11 wherein the positioner is an O-ring retained in resiliently deformed condition in the pusher tube.

13. The combination of claim 10 including a gage flange on the inserter tube to engage the body and limit insertion of the inserter tube into the lower bowel.

14. The combination of claim 10 including stop means on said tubes to limit said forward displacement of the pusher tube in the inserter tube.

15. The combination of claim 10 wherein the pouch has a closed end to be pulled away from the inserter tube by retraction of the pusher tube, to distend the pouch lengthwise.

* * * * *